United States Patent [19]

Lombardo

[11] Patent Number: 5,057,100
[45] Date of Patent: Oct. 15, 1991

[54] LASER HEAD AND MICROSCOPE ATTACHMENT ASSEMBLY WITH SWIVEL CAPABILITY

[75] Inventor: Igino Lombardo, Sharon, Mass.

[73] Assignee: I.L. Med., Inc., Walpole, Mass.

[21] Appl. No.: 383,852

[22] Filed: Jul. 21, 1989

Related U.S. Application Data

[63] Continuation-in-part of Ser. No. 179,819, Apr. 11, 1988, Pat. No. 4,856,512.

[51] Int. Cl.⁵ .............................................. A61B 17/36
[52] U.S. Cl. ................................ 606/17; 606/18; 219/121.74; 219/121.75
[58] Field of Search ............................. 606/13, 17, 18; 128/395, 396; 219/121.74, 121.75; 372/108

[56] References Cited

U.S. PATENT DOCUMENTS

| | | | |
|---|---|---|---|
| 3,084,694 | 4/1963 | Kavanagh et al. | 606/18 X |
| 3,348,547 | 10/1967 | Kavanagh | 128/395 |
| 3,796,220 | 3/1974 | Bredemeier | 606/18 |
| 4,491,131 | 1/1985 | Vassiliedis | 606/18 X |
| 4,494,540 | 1/1985 | Erb | 606/18 |

Primary Examiner—Lee S. Cohen
Attorney, Agent, or Firm—Weingarten, Schurgin, Gagnebin & Hayes

[57] ABSTRACT

A microscope attachment assembly is provided for pivotably mounting a surgical laser to a microscope. A micromanipulator housing is adapted to swing away to an off-axis position to facilitate exchanging the objective lens of the microscope. The spot size of the laser is controlled by shifting the position of a field lens included in a field lens assembly which is shifted along the laser beam by a stepper motor. By toggling a cut-/coagulate switch, the field lens is moved between a presetable cut-mode position and a presetable coagulate-mode position.

13 Claims, 7 Drawing Sheets

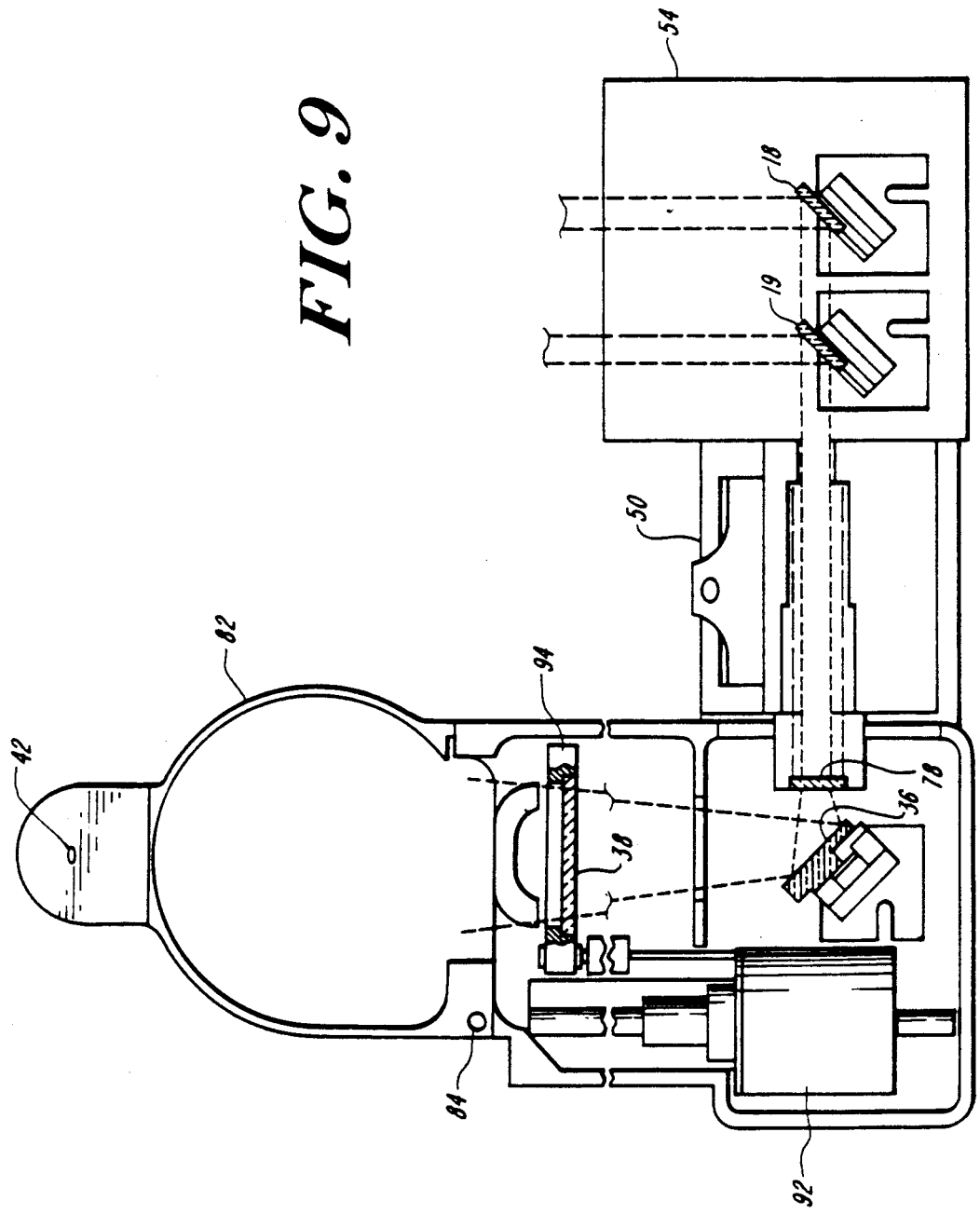

LASER HEAD AND MICROSCOPE ATTACHMENT ASSEMBLY WITH SWIVEL CAPABILITY

This application is a continuation-in-part of application Serial No. 07/179,819, filed on Apr. 11, 1988, now U.S. Pat. No. 4,856,512, and assigned to the same assignee as the instant invention.

FIELD OF THE INVENTION

The present invention relates to a surgical laser system and more particularly to a mounting assembly for adjustable attachment of a laser to a surgical microscope.

BACKGROUND OF THE INVENTION

In microsurgical applications, a surgical laser may be used in conjunction with a surgical microscope. Small laser heads have been developed which can mount directly to a surgical microscope usually by attaching directly to the standard microscope dovetail mount or to the standard microscope objective lens mount. Two types of microscope mounted lasers have been used. Some are mounted with the laser extending at about 90° with respect to the microscope optical axis and others are mounted with the laser extending parallel to the microscope optical axis.

The laser and its optical train are configured in a package which is generally quite sizeable and in certain circumstances interfere with the surgical procedure or with the movement of the microscope and its attached laser about the surgical field. Sometimes the laser will interfere with the view of the surgical site or will otherwise interfere with the access to the surgical site by the various personnel required to do the operation. Under some conditions a laser mounted at 90° to the optical axis offers advantages, while in other conditions, the parallel mounted laser provides advantages.

In the past, before compact lasers were mounted directly to the microscope, the laser was positioned remote from the microscope and the laser beam was delivered to the microscope through the articulated arm on which the microscope was supported. Such lasers are shown, for example, in U.S. Pat. No. 4,309,998 and U.S. Pat. No. 4,122,853. To permit transmission of the laser energy through the articulated arm, the arm must be hollow and a series of special joints and mirrors are used to deliver the beam to the surgical site. Every time the articulated arm is moved, there is a possibility that the lenses in the joints can become misaligned. If a large number of lenses are used the misalignments of the multiple lenses can require constant readjustment of the articulated arm and laser beam path.

It would be desirable to have a compact laser mounted directly to a microscope which could be swiveled from a position aligned perpendicular to the optical axis of the microscope to a position aligned parallel to the optical axis of the microscope or to a variety of other positions. It would further be useful to have such a swiveling laser mount which would not need constant realignment and adjustment of the lenses in the assembly.

It is also desirable for a user to have access to the objective lens of the microscope during use for cleaning or other purposes.

Additionally, it is desirable for a user to be able to set and recall various laser spot sizes for a variety of surgical tasks.

SUMMARY OF THE INVENTION

The present invention provides a microscope attachment assembly for pivotably mounting a surgical laser head relative to a microscope. The assembly includes a microscope platform and mounting apparatus, which preferably mates with the existing dovetail bracket of the typical microscope. An opening in the microscope platform is aligned with the objective lens of the microscope so that when the microscope platform is mounted on the microscope the user has an unobstructed view of the surgical site below the microscope. A micromanipulator housing is adapted to swing away to an off-axis position to facilitate exchanging objectives. A first collar extends from the platform. A second collar fits within the first collar and supports the laser. There are rotational locking apparatus on the first and second collars so that the laser may be selectively positioned at various rotational alignments with the optical axis of the microscope. There may also be an axial locking mechanism for preventing the two collars from moving axially with respect to one another.

In the preferred embodiment, the rotational locking means includes a series of detent balls on one collar and a series of detent recesses on a confronting surface of the other collar which cooperate to hold the collars in a desired rotational orientation with respect to one another.

The axial locking mechanism can be another series of detent balls fitting into one or more detent grooves on the collars. The length of the detent grooves could be aligned with the two preferred positions of the rotational locking means to provide a stop for preventing rotation beyond the preferred positions. In one position the laser is oriented parallel to the optical axis of the microscope. In the other position the laser is oriented perpendicular to the optical axis of the microscope.

To minimize the optical misalignment of the laser beam with the focusing lenses, the principle negative focusing lens is mounted in the second collar so that its position with respect to the laser beam does not change when the laser is swiveled with respect to the microscope platform. A second focusing lens is mounted in the first collar or in the microscope platform. The second lens is intended to match the focal point of the laser beam with that of the objective lens of the microscope. Also the second lens can be used to vary the size of the laser beam at the focal plane of the microscope. The principal negative focusing lens can also be used for the same purpose.

The focusing lenses discussed above may each be comprises of one or more optical elements depending on the desired correction of chromatic and spherical aberrations. Correction for these aberrations are well known in the art. Correction of achromatic aberrations can be achieved for all wavelengths and depends only on availability of suitable glasses. In the infrared region, and for $CO_2$ lasers, chromatic aberration correction has some practical limitations since the suitable glasses are to some degree water soluble.

The spot size of the laser is controlled by shifting the position of a field lens. The field lens is part of a field lens assembly, and is moved preferably by an associated stepper motor. In addition, by toggling a cut/coagulate switch, a user can selectively move the field lens to a presetable cut-mode position or a presetable coagulate-mode position.

These and other features and advantages of the present invention will become apparent from the following detailed description of the preferred embodiments taken in conjunction with the following drawings.

BRIEF DESCRIPTION OF THE DRAWINGS

FIG. 9 is a schematic view of the present invention including a stepper motor, field lens assembly and the micromanipulator housing of FIGS. 8A & 8B;

DETAILED DESCRIPTION OF THE PREFERRED EMBODIMENT

Figure 2:
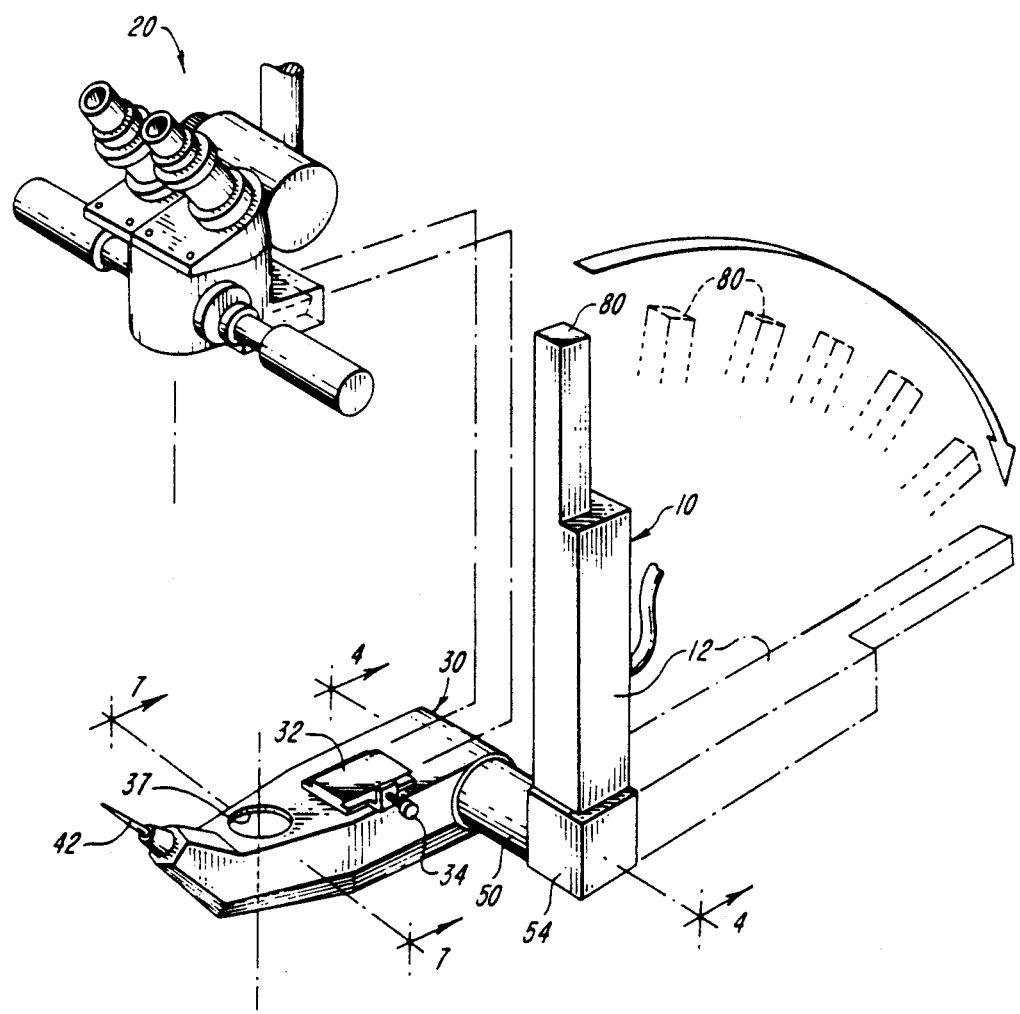
FIG. 2 shows an exploded perspective view of the microscope platform with the microscope and laser attached.
Figure 7:
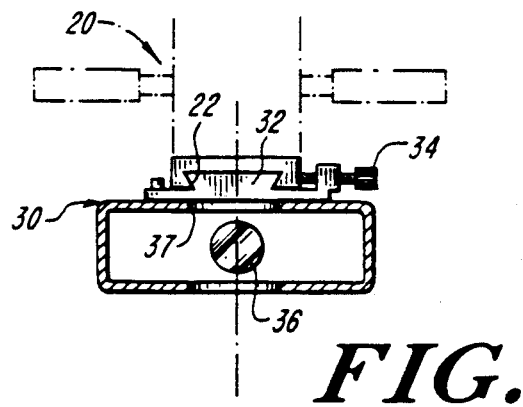
FIG. 7 is a partial cross-sectional view taken along line 7—7 in FIG. 2 showing the mounting of the microscope on the platform.

Referring to FIG. 2, there is shown a laser 10, a microscope 20, and a microscope platform 30. A standard microscope dovetail 22 (see FIG. 7) connects to a corresponding dovetail ways 32 on microscope platform 30. Dovetail locking screw 34 locks microscope 20 onto dovetail ways 32.

Figure 1:
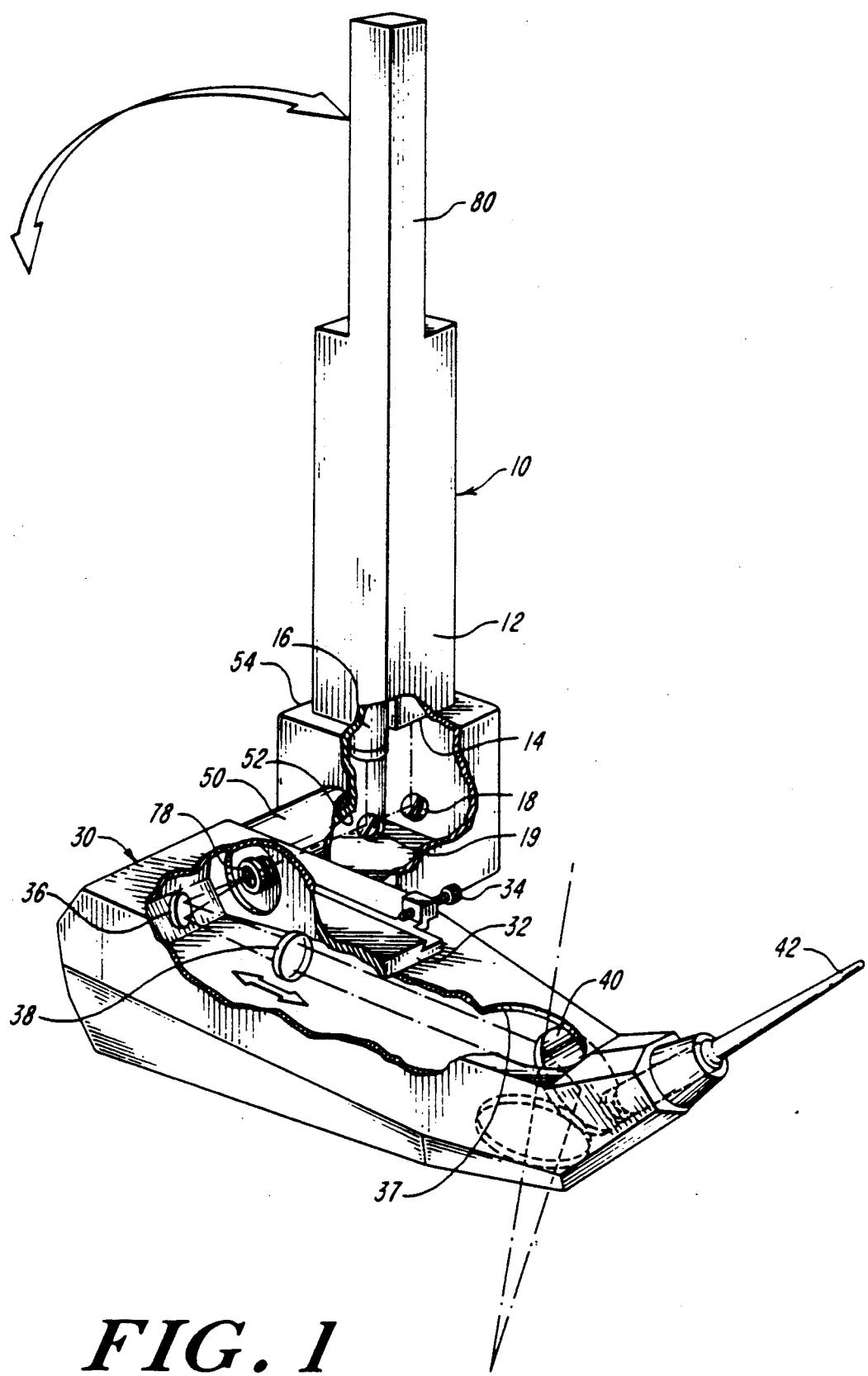
FIG. 1 shows a perspective view, partly in section of the present invention, the platform of the present invention with the laser attached and schematically showing major elements of the optical lenses used to transmit the laser beam through the platform with the laser aligned generally parallel to the optical axis of the microscope.

With reference to FIG. 1, laser 10 is encased in laser housing 12 which encloses an operating laser 14, for example a carbon dioxide laser, and a targeting laser 16, for example a helium-neon laser, with appropriate optics which can include a deflecting mirror 18 and a beam combiner 19 for jointly transmitting the helium-neon and the carbon dioxide laser beams.

Microscope platform 30 encloses a deflecting mirror 36 which directs the laser beams toward an adjustable mirror 40 and an adjustable field lens 38. The mirror 40 can be manipulated by a manually operated joy stick 42 or alternatively could be adjusted automatically through a motor driven system (not shown).

Adjustable field lens 38 is intended to adjust the focal point of the laser beam generally to the focal length of the objective lens of the microscope so that the laser beam will be focused at approximately the same focal plane that the surgeon views through the microscope. This lens is also preferably used to defocus the laser beam so that a variety of laser beam spot sizes can be achieved at the focal plane of the microscope. Most microscopes are equipped with a variety of objective lenses so that the surgeon can adjust the working distance of the microscope from the surgical site. The position of the field lens 38 must correspond to each different objective lens of the surgeon's microscope.

Figure 10:
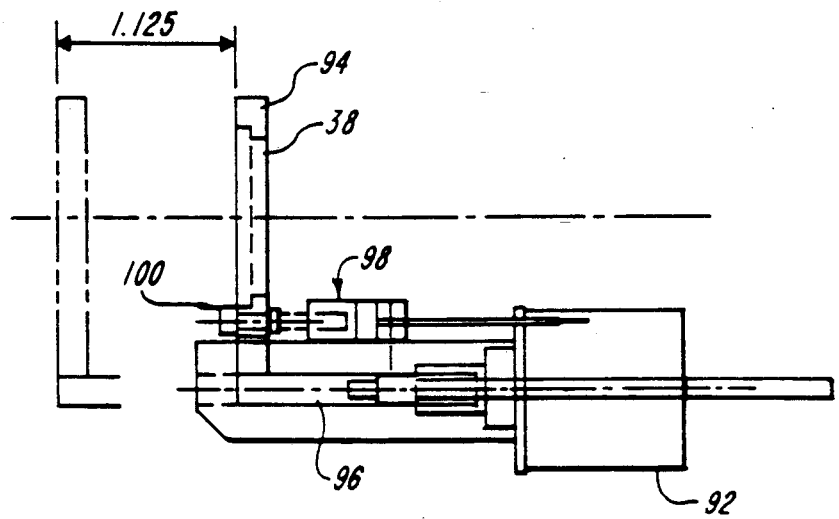
FIG. 10 is a schematic view of a stepper motor and a field lens assembly showing its near-travel-limit and its far-travel-limit.

In a preferred embodiment, the field lens 38 is positioned using a stepper motor 92, as shown in FIGS. 9 and 10. The field lens 38 is held by a lens holder 94 which is rigidly fixed to a shaft 96 which is extended by the stepper motor 92. A suitable stepper motor is the AIRPAX model L92121-P2 servo motor with ball screw. A photoswitch 98 is used to detect the near-travel-limit of the lens holder 94. When at its near-travel-limit, a switch actuator screw 100 obstructs the light beam of photoswitch 98 which provides a signal to motor control circuitry 114 (FIG. 11), which then stops the travel of the lens holder 94. The far-travel-limit is enforced by an internal mechanical stop (not shown). The lens holder 94 travels a distance of 1.125 inches between its travel limits.

The laser system of the invention can be used for dermatalogic surgery; plastic surgery; ear, nose and throat surgery; neurosurgery and any other surgical procedure requiring high precision in spot size and targeting. A laser beam's ability to affect a region of tissue is expressed as a power density, i.e., power per unit area in watts per square centimeter. Assuming a constant power laser pulse, the total effect of the pulse is the product of its power density and duration. The area in square centimeters of a circular spot expressed in terms of its diameter in millimeters is $\pi D^2/400$ where $\pi = 3.14159\ldots$, and D is the diameter of the spot in millimeters. Thus, power density Pd is equal to the power P divided by the area in square centimeters, i.e., $$Pd = (400/\pi D^2) * P.$$

Since power density Pd is inversely related to spot size D, as spot size D increases (as when a laser beam is defocused), the power density decreases. Conversely, decreasing the spot size D increases the power delivered to the exposed region of tissue, with a consequent increase in tissue damage. If it is necessary to maintain a substantially equal spot size both before and after the objective lens 90 of the microscope 22 is exchanged, the field lens 38 must be moved to compensate for the different focal length of the replacement objective lens. Representative focal objective lengths include 250 mm, 300 mm and 400 mm, and representative spot sizes include 0.2 mm, 0.3 mm, 0.4 mm, and up to 2.0 mm increments of 0.1 mm.

If a greater or lesser power density at the tissue site is required, the field lens must be moved to respectively decrease or increase the spot size. In particular, in a cut mode, the selected spot size results in an optimum rate of tissue destruction. After cutting tissue, it is often necessary to promote coagulation of the resultant blood that flows from the surrounding capillaries and other small blood vessels.

The power density required for coagulating blood is less than the power density required for cutting tissue. Thus, in coagulation mode, the spot size must be larger than the cut-mode spot size for a given laser power setting. While cutting tissue, it is sometimes necessary to interrupt cutting, promptly begin coagulating the resultant blood flow, and resume outting tissue using the original power level of the laser beam. To rapidly change power density at the tissue site, the spot size is changed by quickly shifting the field lens 38. For each objective lens of different focal length, an optimal cut-mode field lens position value is stored in a standard memory device included in a microcomputer 110 shown in FIG. 11. An optimal coagulate-mode field lens position value is also stored for each different objective lens.

Figure 11:
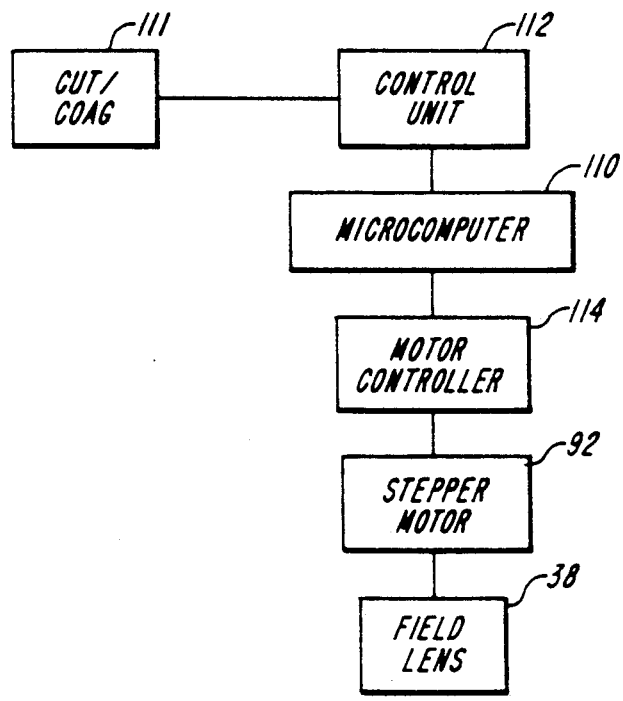
FIG. 11 is a functional block diagram of the field lens control apparatus.

Referring to FIG. 11, to switch between cut-mode and coagulate-mode, a user activates a switch 111 on a control unit 112 which provides a signal to the microcomputer 110, which provides a signal to a motor controller 114 in accordance with other setting information stored in the microcomputer 110, such as the focal lengths of the objective lenses. The motor controller 114 controls the stepper motor 92 shown in FIG. 9, which shifts the fields lens 38 along the path of the laser beam.

To provide precision targeting of the laser spot, an adjustable mirror 40 and a joystick 42 are used to direct the focused laser beam about the surgical surface.

Figure 8A:
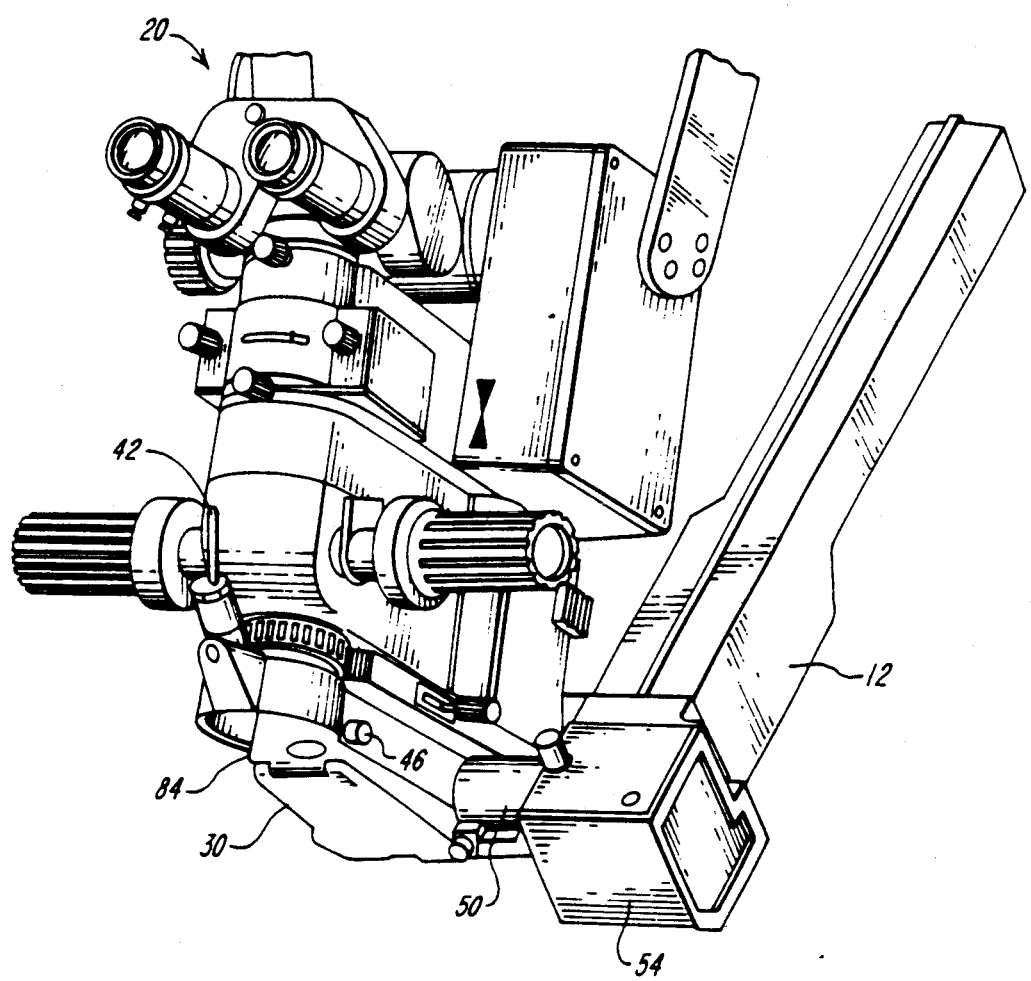
FIG. 8A is a perspective view of an embodiment of the present invention including a micromanipulator housing adapted to swing into an off-axis position.
Figure 8B:
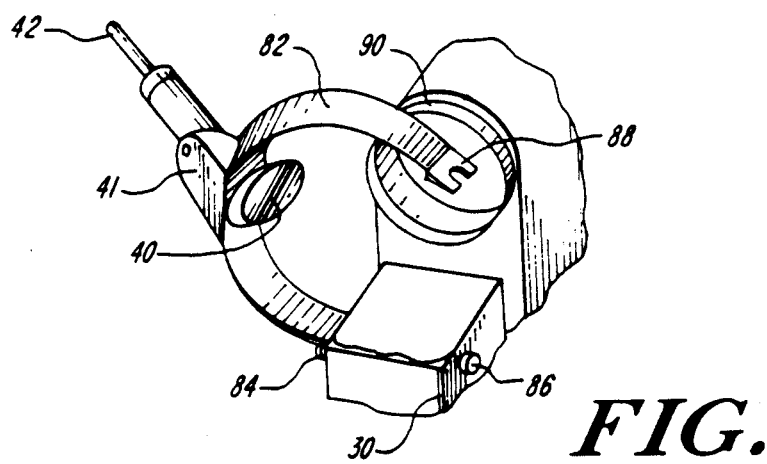
FIG. 8B is a perspective view of the micromanipulator of FIG. 8A in an off-axis position.

Referring to FIGS. 8A and 8B, in another preferred embodiment of the present invention, the joystick 42 extends through a housing section 41 that is disposed between the ends of the bridged swivel case 82 The distal end of the joystick 42 is connected to the mirror in a manner that allows macromanipulations of the proximal end of the joystick 42 to result in micromovements of the mirror 40. As in the embodiment of FIG. 1, the mirror 40 can be manipulated by the manually operated joystick 42. To change or clean the microscope's objective lens 90, the bridged swivel case 82 can be pivoted about a pin 84 that is fixed to a side of the microscope platform 30, into an off-axis position as shown in FIG. 8B. To fix the swivel case 82 into an operating position as shown in FIG. 8A, a forked end 88 of the swivel case 82 is engaged with the shaft of a thumbscrew 86, the shaft being fixed to a side opposing the side to which the pin 84 is affixed. The thumbscrew 86 is then tightened manually.

Referring again to FIG. 1 it can be seen that a first preferably cylindrical collar 50 extends from microscope platform 30 and receives a second preferably cylindrical collar 52 extending from the output end 54 of laser housing 12.

Figure 3:
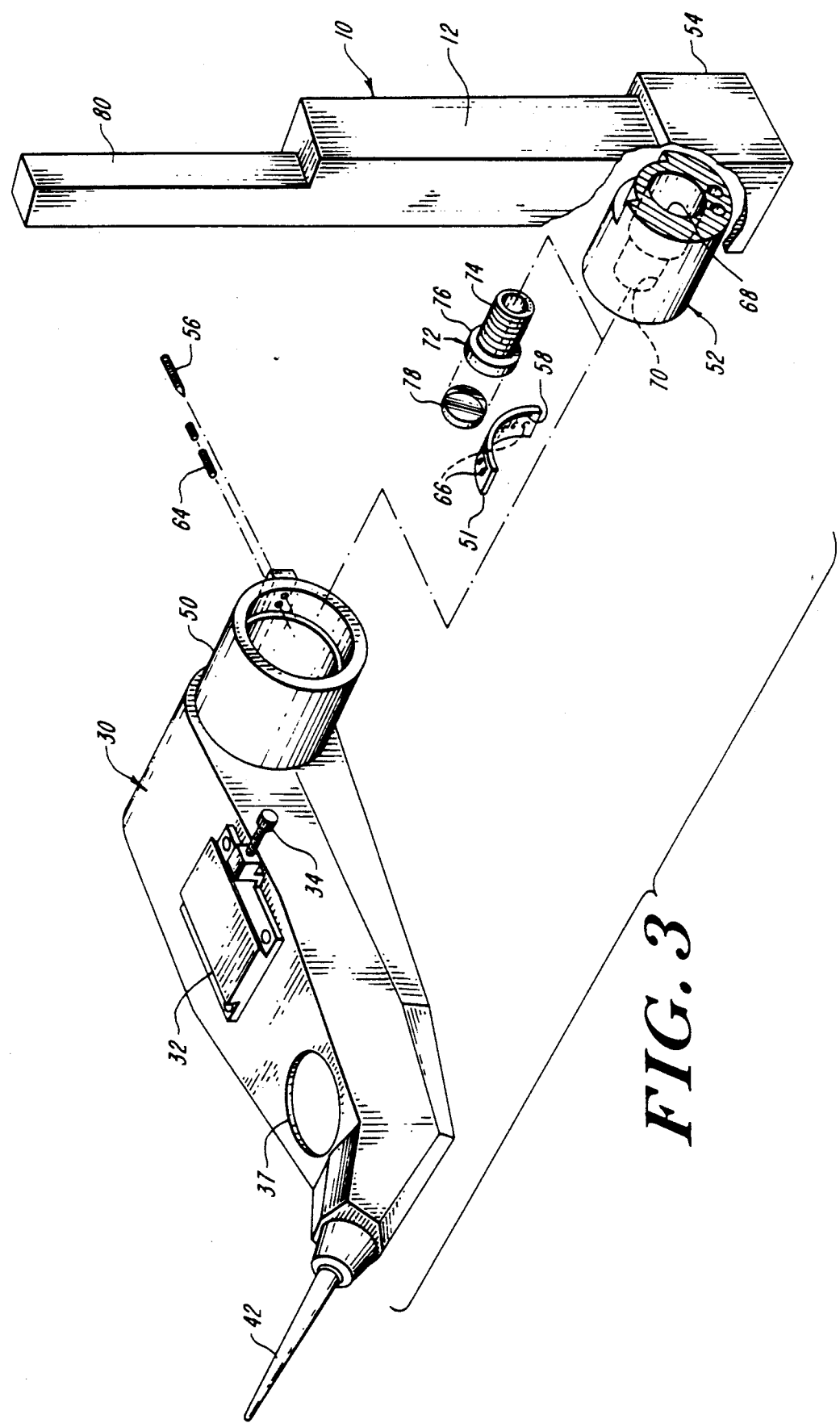
FIG. 3 shows an exploded perspective view of the present invention partly in section.

Referring now to FIG. 3, there is shown an exploded perspective of the microscope attachment assembly of the present invention including laser 10 and microscope platform 30 and showing details of the swivel mechanism associated with first collar 50 and second collar 52. A cone point set screw 56 is threaded through the wall of first collar 50. A slot 58 for receiving the end of set screw 56 is placed on the outside surface of rotary joint segment 51 and aligned with set screw 56. Preferably slot 58 extends 90° about the circumference of joint segment 51 and has end walls 60 and 62 (see FIG. 5) to act as stops in conjunction with set screw 56 to hold second collar 52 and laser 10 to which it is rigidly attached in either a parallel alignment with the optical axis of the microscope or in perpendicular alignment with the optical axis of the microscope. Also the interaction of set screw 56 with slot 58 prevents axially motion of collars 50 and 52 with respect to one another. Alternatively, the positions of set screw 56 and slot 58 could be reversed with set screw 56 being mounted on collar 52 or joint segment 51 and slot 58 being mounted on collar 50.

Still referring to FIG. 3, the preferred mechanism for locking laser 10 in various rotational positions with respect to microscope platform 30 is shown. Collar 50 includes a spring loaded detent ball 64 projecting through the wall of collar 50 at a point spaced axially apart from set screw 56 but preferably circumstantially adjacent set screw 56. A series of detent holes 66 project into the outside surface of rotary joint segment 51 aligned with detent ball 64. There are preferably six detent holes spaced equally angularly apart about a 90° arc of the circumference of segment 51. In the preferred embodiment there are six detent holes spaced 18° apart so that laser 10 may be locked in a variety of positions 18° apart from one another with respect to the optical axis of the microscope. Alternatively, the location of detent ball 64 and detent hole 66 could be reversed so that they appear respectively on segment 51 and first collar 50. Also the number and location of detent holes 66 and the length of slot 58 can be changed to cover different angular increments.

Still referring to FIG. 3, we will now describe the mounting of the optical lenses within the microscope attachment assembly so as to minimize the misalignment of the optical lenses as the laser is swiveled from one position to another with respect to the optical axis of the microscope.

A portion of the interior surface 68 of second collar 52 contains threads 70. An annular lens mount 72 has corresponding threads 74 on its exterior circumferential surface. Lens mount 72 can be fixed in any position along the axially extent of threaded surface 68 by using well known locking mechanisms (not shown) but lens mount 72 will not extend axially into collar 52 any further than flange 76 permits. The position of lens mount 72 may be set in the factory and may be later adjusted in the field if necessary. A lens or lens system 78 is mounted in lens mount 72 by conventional means and is fixed in position in collar 52 with respect to laser 14 so that as laser housing 12 rotates from one position to another, lens 78 will stay in a fixed relationship with respect to the beams of lasers 14 and 16, deflector 18 and beam combiner 19 (see FIG. 1). Thus, misalignment of the optical path of the lenses during swiveling will be minimized.

The relationship between the laser beams and diverging lens 78 is extremely important for the proper alignment of the optical path. Having lens 78, which is typically a diverging lens, fixed with respect to the beam path of lasers 14 and 16 provides an important feature of the present invention which permits the laser to be swiveled with a minimum risk of misaligning the optical path. This is a significant improvement over passing the laser beam through a complexed optical path associated with the articulating arm assembly typical of many existing surgical laser systems.

Figure 4:
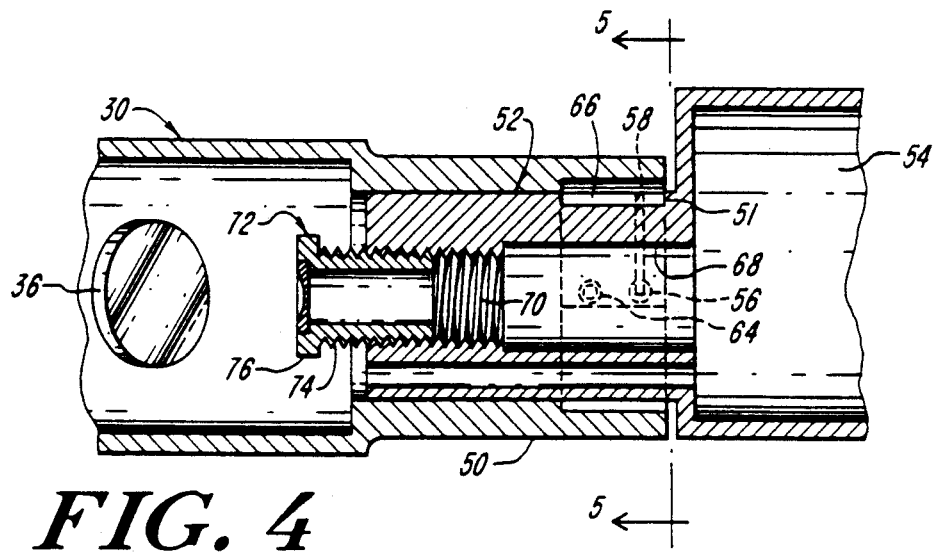
FIG. 4 shows a section view of the collars connecting the laser and microscope platform taken along line 4—4 in FIG. 2.
Figure 5:
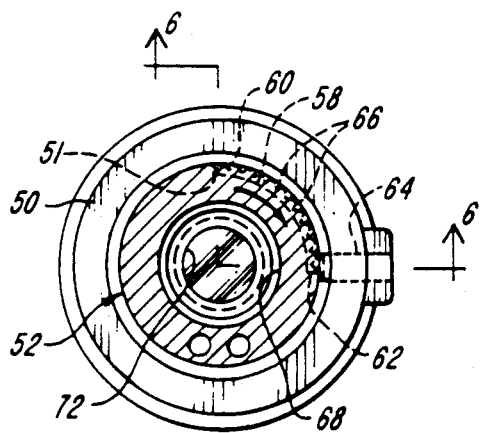
FIG. 5 is a cross-sectional view of the collar and lens arrangement of FIG. 4 taken along 5—5 of FIG. 4.
Figure 6:
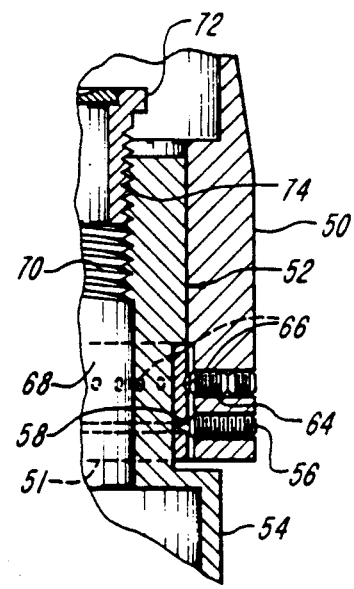
FIG. 6 is a partial cross-sectional view of the collars of FIGS. 4 and 5 taken along line 6—6 in FIG. 5 and showing the detent mechanism.

Referring to FIGS. 4 through 6, the preferred method for joining collars 50 and 52 is shown in cross-sectional detail. In FIG. 4 the second collar 52 is concentrically engaged inside the first collar 50. The lens mount 72 containing lens 78 is threaded into the interior 68 of the second collar 52. Lens 78 is thus seen to be aligned with deflecting mirror 36 in the platform 30.

FIG. 5 shows the concentric arrangement of collars 50 and 52, lens 78 and the laser beam path. The laser beam is directed through collars 50 and 52 and the center of lens 78, as explained in conjunction with FIG.

1. Collars 50 and 52 may move in a radial arc relative to each other, as delimited by the end walls 60 and 62 of the slot 58 into which set screw 56 extends. As collar 52 and laser housing 12 are rotated about the laser beam axis in collars 50 and 52, detent holes 66 and detent ball 64 provide detent position at discrete intervals around a rotational arc. Set screw 56 and spring loaded detent ball 64 are more clearly shown in FIG. 6, and are seen to be aligned with their respective slot and holes in the rotary joint segment 51. Alternatively, the entire detent mechanism can be replaced with friction rings (not shown) or a number of motorized means (not shown) and a number of other well known means for providing controlled rotation between two mating parts.

The coaxial alignment of collars 50 and 52 with the laser beam path, illustrated in FIG. 5, shows why the assembly of the present invention minimizes laser beam misalignment as the laser housing 12 is moved. Movement of laser housing results only in radial movement of the concentric collars 50 and 52. Since this movement is constrained to rotational pivoting about the laser beam path, there is no off-axis motion which can misalign the optical train, as there is when an articulated arm assembly with reflecting mirrors at the joints is moved.

In use the microscope attachment assembly of the present invention is mounted to an existing microscope 20 as shown in FIG. 2. The microscope is generally equipped with a microscope arm and counter balance system (not shown). With the microscope platform 30 attached to microscope 20 by means of dovetail groove 22, dovetail platform 32 and dovetail locking screw 34, the optical axis of the microscope will be generally aligned above opening 37 in platform 30. The adjustable field lens is adjusted to match the objective lens of the microscope so that the laser beam will be focused in the focal plane of the microscope objective lens. In FIG. 2 laser housing 12 is shown aligned generally parallel to the optical axis of the microscope. The user may conveniently move laser housing 12 to a different rotational position by grasping the projection 80 housing and pushing laser housing 12 away from him. The rotational locking mechanism which includes detent ball 64 and the series of detent holes 66 will hold laser housing 12 in a variety of rotational positions (shown in phantom) between the two extremes of alignment parallel to or perpendicular to the optical axis of the microscope.

It will be noted that the optical path of the laser beam from lasers 14 and 16 will not change radially when laser housing 12 is rotated, but will merely pivot where the optical path passes through the concentric collars 50 and 52.

Thus, if the operating surgeon finds that the position of laser housing 12 is awkward or presents an obstacle to the surgical field, one can simply rotate laser housing 12 to a more convenient position. The optics will not change during the rotation and neither the laser optics nor the optics of the microscope need be adjusted. The rotation of laser housing 12 may be accomplished with minimal interruption and with maximum convenience.

It will be appreciated that the microscope attachment assembly of the present invention is particularly well suited to speedy and convenient adjustment of the orientation of laser housing 12 with respect to the optical axis of microscope 20. The adjustment can be accomplished with minimum interruption and minimum misalignment of the laser and visual optical paths so that surgical personnel can conveniently adjust the physical location of their instruments with minimum interruption during the surgical procedure.

The present invention has been described in conjunction with certain preferred embodiments. Those skilled in the art will appreciate that many modifications and changes may be made to the preferred embodiments without departing from the scope of the present invention. It is, therefore, not intended to limit the present invention except as set forth in the appended claims.

What is claimed is:

1. A laser assembly for mounting a surgical laser to a surgical microscope over an operative area, and for directing a surgical laser beam into a surgical field of the microscope, comprising:

a microscope platform capable of receiving a laser beam at an entrance point and directing the beam through the microscope platform out to a desired point within the surgical field of the microscope;

said microscope platform including mounting means attached to the microscope platform and being pivotably movable between a closed and an open position, and mirror means including a mirror, coupled to the mounting means, and operative to direct the laser beam to selectable points in the surgical field of the microscope;

the mounting means in the closed position being operative to dispose the mirror means in the path of the laser beam for selectable direction of the laser beam within the surgical field, and being operative in the open position to permit access to an objective lens of the surgical microscope.

2. The laser assembly of claim 1 wherein the mirror of said mirror means is coupled to an adjusting means that is mounted on said mounting means, the adjusting means being operative to adjust the position of the mirror for selected direction of the laser beam to a selected region within the surgical field of the microscope.

3. The laser assembly of claim 2 wherein the adjusting means is a micromanipulator.

4. The laser assembly of claim 1 wherein the mounting means includes a C-shaped member having one end pivotably attached to the microscope platform, and the other end having joining means for joining with a receiving member on the microscope platform.

5. The laser assembly of claim 4 wherein the C-shaped member includes a housing section disposed between the ends of the C-shaped member, and having adjusting means mounted thereto, the adjusting means being connected to said mirror of the mirror means and operative to adjust the mirror to direct the laser beam to selectable points in the surgical field.

6. A laser assembly for mounting a surgical laser to a surgical microscope over an operative area, and for directing a surgical laser beam into a surgical field of the microscope, comprising:

a microscope platform capable of receiving a laser beam at an entrance point and directing the beam through the microscope platform out to a desired point within the surgical field of microscope, wherein said microscope platform including an optical assembly adjustable to selectively provide a plurality of laser spot sizes within the surgical field of the microscope, wherein the optical assembly includes a field lens disposed in an optical path of a laser beam, means for moving the field lens along the path of the laser beam, and means for moving the field lens to select positions to provide selectable laser beam spot sizes, and wherein the means for moving the field lens along the optical path of the laser beam includes electrically controlled motor means for inducing mition of said optical assembly.

7. The laser assembly of claim 6 wherein the means for moving the field lens to selected positions includes a control means and a control switch for selecting spot size according to the setting of said control switch, for each objective lens of a given focal length.

8. The laser assembly of claim 7 wherein the means for moving the field lens includes means defining an adjustment path, means for mounting the field lens, and motive means for moving the field lens along the adjustment path.

9. The laser assembly of claim 8 wherein the motive means includes a stepper motor.

10. The laser assembly of claim 9 wherein the motive means includes a stepper motor and control means for selected operation of the stepper motor.

11. The laser assembly of claim 10 wherein the control means include a cut/coagulate switch for causing movement of the field lens to respective positions in accordance with the setting of the switch to provide a laser beam spot size appropriate for either a cutting or coagulating mode of operation.

12. The laser assembly of claim 11 wherein the control means include a bimodal switch for causing movement of the field lens to respective positions in accordance with the setting of the switch to provide a laser beam spot size appropriate for either a 1st or 2nd mode of operation.

13. A laser assembly for mounting a surgical laser to a surgical microscope over an operative area, and for directing a surgical laser beam into a surgical field of the microscope, comprising:

a microscope platform capable of receiving a laser beam at an entrance point and directing the beam through the microscope platform out to a desired point within the surgical field of the microscope;

said microscope platform including an optical assembly adjustable to selectively provide a plurality of laser spot sizes within the surgical field of the microscope;

said microscope platform also including mounting means attached to the microscope platform and being pivotably movable between a closed and an open position, and mirror means coupled to the mounting means and operative to direct the laser beam to selectable points in the surgical field of the microscope;

the mounting means in the closed position being operative to dispose the mirror measuring the path of the laser beam for selectable direction of the laser beam within the surgical field, and being operative in the open position to permit access to an objective lens of the surgical microscope.

* * * * *

UNITED STATES PATENT AND TRADEMARK OFFICE
CERTIFICATE OF CORRECTION

PATENT NO.    : 5,057,100
DATED         : October 15, 1991
INVENTOR(S)   : Igino Lombardo It is certified that error appears in the above-identified patent and that said Letters Patent is hereby corrected as shown below:

Column 2, line 53, "comprises" should read --comprised--.

Column 2, line 56, "achromatic" should read --a chromatic--.

Column 4, line 8, "surgeon s" should read --surgeon's--.

Column 4, line 9, "38 is Positioned" should read --38 is positioned--.

Column 5, line 27, "case 82 The" should read --case 82. The--.

Column 6, line 8, "circumstantially" should read --circumferentially--.

Column 8, line 68, "to select" should read --to selected--.

Column 9, line 5, "mition" should read --motion--.

Column 10, line 24, "the mirror measuring the path of" should read --the mirror means in the path of--.

Signed and Sealed this

Twenty-sixth Day of October, 1993

Attest:

BRUCE LEHMAN

Attesting Officer

Commissioner of Patents and Trademarks